United States Patent [19]
Pritchard et al.

[11] 4,405,306
[45] Sep. 20, 1983

[54] MEDICATED DISPOSABLE DOUCHE PRODUCT

[75] Inventors: Robert W. Pritchard, Pittsburgh, Pa.; Edward J. Drozd, Lake Hiawatha; Michael K. Lutz, Watchung, both of N.J.

[73] Assignee: Beecham Inc., Clifton, N.J.

[21] Appl. No.: 328,734

[22] Filed: Dec. 8, 1981

[51] Int. Cl.³ .............................................. A61M 1/00
[52] U.S. Cl. ................................................... 604/87
[58] Field of Search .................. 128/232, 272.1, 224, 128/251; 206/219, 221; 215/6

[56] References Cited

U.S. PATENT DOCUMENTS

| | | | |
|---|---|---|---|
| 3,354,883 | 11/1967 | Southerland | 128/232 |
| 3,924,741 | 12/1975 | Kachur et al. | 206/221 |
| 4,122,943 | 10/1978 | Silver et al. | 128/272.1 X |
| 4,194,640 | 3/1980 | Crankshaw et al. | 128/272.1 X |

Primary Examiner—John D. Yasko
Attorney, Agent, or Firm—Jacobs & Jacobs

[57] ABSTRACT

A douche product which comprises a bottle filled with a douching liquid, a reservoir in the bottle containing a liquid to be mixed with the douching liquid and a nozzle attached to the bottle for dispensing the contents of the bottle, the nozzle and the reservoir having cooperating devices so that the reservoir may be opened to permit the contents thereof to drain into the bottle when the nozzle is moved relative to the bottle.

9 Claims, 8 Drawing Figures

MEDICATED DISPOSABLE DOUCHE PRODUCT

The present invention relates to disposable douche products, more particularly to a product adapted to dispense a medicated douche liquid.

Disposable douche products are known wherein a douche liquid is contained within a flexible plastic container, and a separate ampoule containing a medicament is provided. A typical medicament is an aqueous solution of providone-iodine. The consumer opens the container, dispenses the contents of the ampoule into the container, mixes the contents and attaches a hollow nozzle or probe. This multi-step procedure is difficult for some consumers to carry out, and in any case, can be messy. Further, there is the risk of spilling the contents of the container after it has been opened and before the probe is attached.

The present invention provides a disposable douche product that requires no disassembly and assembly and no step of adding a medicament. In particular, the douche product of the invention comprises a flexible container filled with a douching liquid, a reservoir filled with a medicament located inside the head of the container, a nozzle threadedly engaging and rotatable about the container head and sealing means for preventing the contents of the reservoir from entering the container and for preventing the contents from flowing out through the nozzle, the nozzle being operable when rotated to open the sealing means to allow the contents of the reservoir to drain into the container for mixing with the liquid therein and to permit the mixture to be dispensed through the nozzle.

The present invention is illustrated in terms of a preferred embodiment in the accompanying drawings, in which:

FIG. 4 is a view in section taken along lines IV—IV in FIG. 2;

FIG. 5 is a view in section taken along lines V—V in FIG. 3;

FIG. 6 is an enlarged elevational view, partly in section, of the reservoir;

FIG. 7 is an enlarged top plan view of a sealing fitment; and

FIG. 8 is a view similar to FIG. 7 of an alternative embodiment of the invention.

Figure 1:
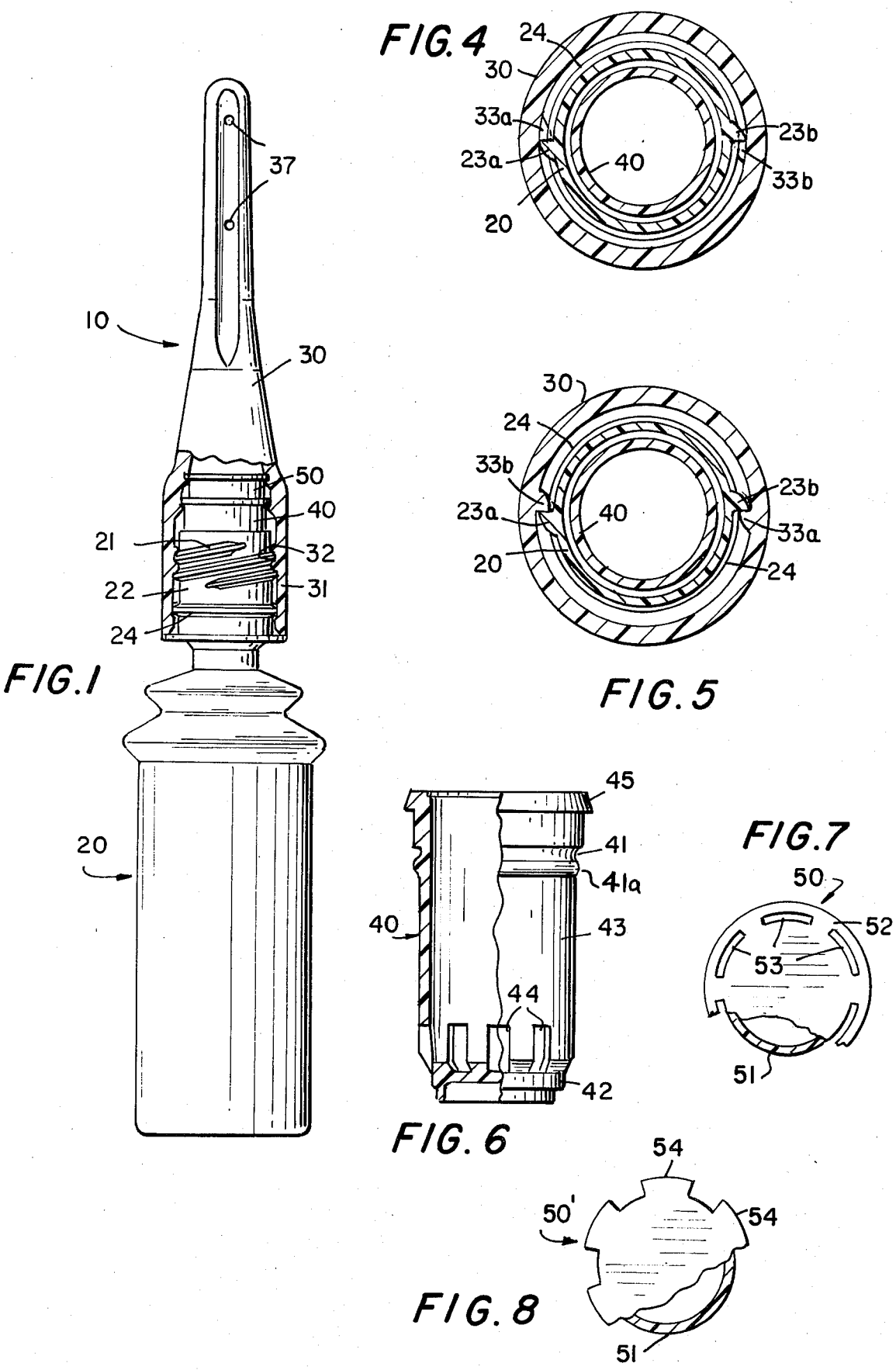
FIG. 1 is an elevational view, partly in section, of the disposable product of the invention in its sealed position.

Referring to FIG. 1 of the drawings, the disposable douche product 10 comprises a bottle 20 filled with a measured amount of a douching liquid, a hollow probe or nozzle 30, a reservoir 40 filled with a medicament, and a sealing fitment 50. Probe 30 is internally tapped at 32 to receive the screw thread 21 carried by head 22 of bottle 20. Probe 30 may thus be screwed onto the head 22 of bottle 20.

Figure 2:
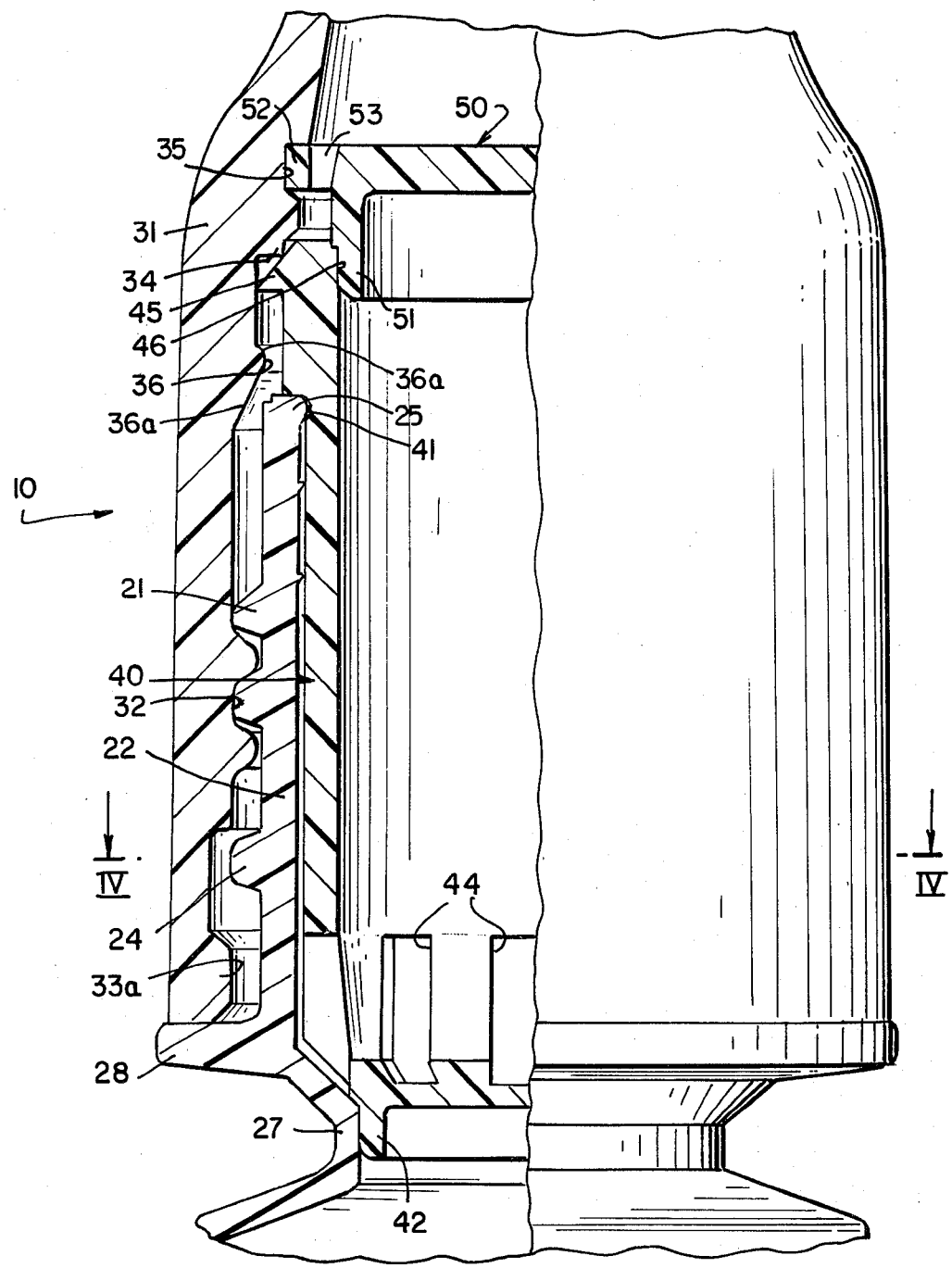
FIG. 2 is an enlarged view, partly in section, of a portion of the douche product, showing the reservoir in its sealed position.

FIG. 2 shows the douche product 10 in its closed and sealed position. As can be seen in FIG. 2, the skirt 31 of probe 30 has diametrically opposed lugs 33a and 33b at its lowermost end. Head 22 of bottle 20 has a pair of diametrically opposed, complementary lugs 23a and 23b (FIG. 4) spaced above lugs 33a and 33b as viewed in FIG. 2. Bottle lugs 23a and 23b are spaced apart 180° on ring 24 (FIGS. 1 and 2).

FIG. 2 also shows the reservoir 40 in sealing engagement with bottle 20, and sealing fitment 50 in sealing engagement with reservoir 40. Thus, reservoir 40 has an internal, circular groove 41 which is engaged by snap ring 25 when reservoir 40 is pushed into place inside bottle 20. The base 42 of reservoir 40 is of smaller diameter than the body portion 43 (FIG. 6), and is press-fit inside the neck portion 27 (FIG. 2) of bottle 20, thus providing a liquid seal. The snap ring 25 and groove 41 will provide an audible "click" when the base 42 enters into sealing engagement with neck 27. Snap ring 25 and groove 41 also help to ensure that the reservoir base 42 and bottle neck 27 do not accidentally come out of sealing engagement. Reservoir 40 has a plurality of circumferentially extending outlet ports 44 that allow fluid communication between the reservoir 40 and bottle 20 when the neck 27 and reservoir base 42 are out of sealing engagement.

Sealing fitment or cover 50 (FIG. 2) is press-fit inside the open top of reservoir 40, with the depending cylindrical wall 51 sealingly engaging the inside wall portion 46 at the top of reservoir 40. With the reservoir 40 thus sealed at top 46, 51 and bottom 42, 27 by sealing fitment 50 and neck 27, respectively, any liquid in reservoir 40 will be safely confined. Sealing fitment 50 has an annular flange 52 (FIG. 7) having a plurality of ports 53 therethrough. Flange 52 is snapped into retaining groove 35 and is thus retained in groove 35 for movement with the probe 30 as will be described hereinafter. FIG. 8 shows an alternative fitment, 50′, which has flange portions 54 that fit into retaining groove 35. Flange portions 54 are spaced apart to permit flow of liquid therebetween and are the functional equivalent of ports 53.

The douche product 10 is assembled as follows. First, bottle 20 is filled with a premeasured amount of a douching liquid. Then reservoir 40 is pressed into the open head 22 of bottle 20 until snap ring 25 snaps into groove 41 thereby ensuring that neck 27 sealingly engages the base 42 of reservoir 40. Reservoir 40 is then filled through its open top with the desired liquid medicament. To complete the filling operation, sealing fitment 50 is pushed into probe 30 until flange 52 snaps into retaining groove 35. The probe 30 with sealing fitment secured thereto is then screwed clockwise (as viewed in FIG. 4) onto bottle 20 by engagement of thread 21 and internal tapping 32. As probe 30 descends relative to the bottle 20, the probe lugs 33a and 33b will ride over the bottle lugs 23a and 23b and assume the position shown in FIG. 2, and the sealing wall 51 will gradually enter and seal the open top of the reservoir 40. Probe 30 is then rotated clockwise until it contacts circular flange 28 (FIG. 2) at the juncture between head 22 and neck 27. Douche product 10 can now be safely stored and transported without fear of leakage of the liquids within reservoir 40 and bottle 20 and without premature mixing of the two liquids.

Figure 3:
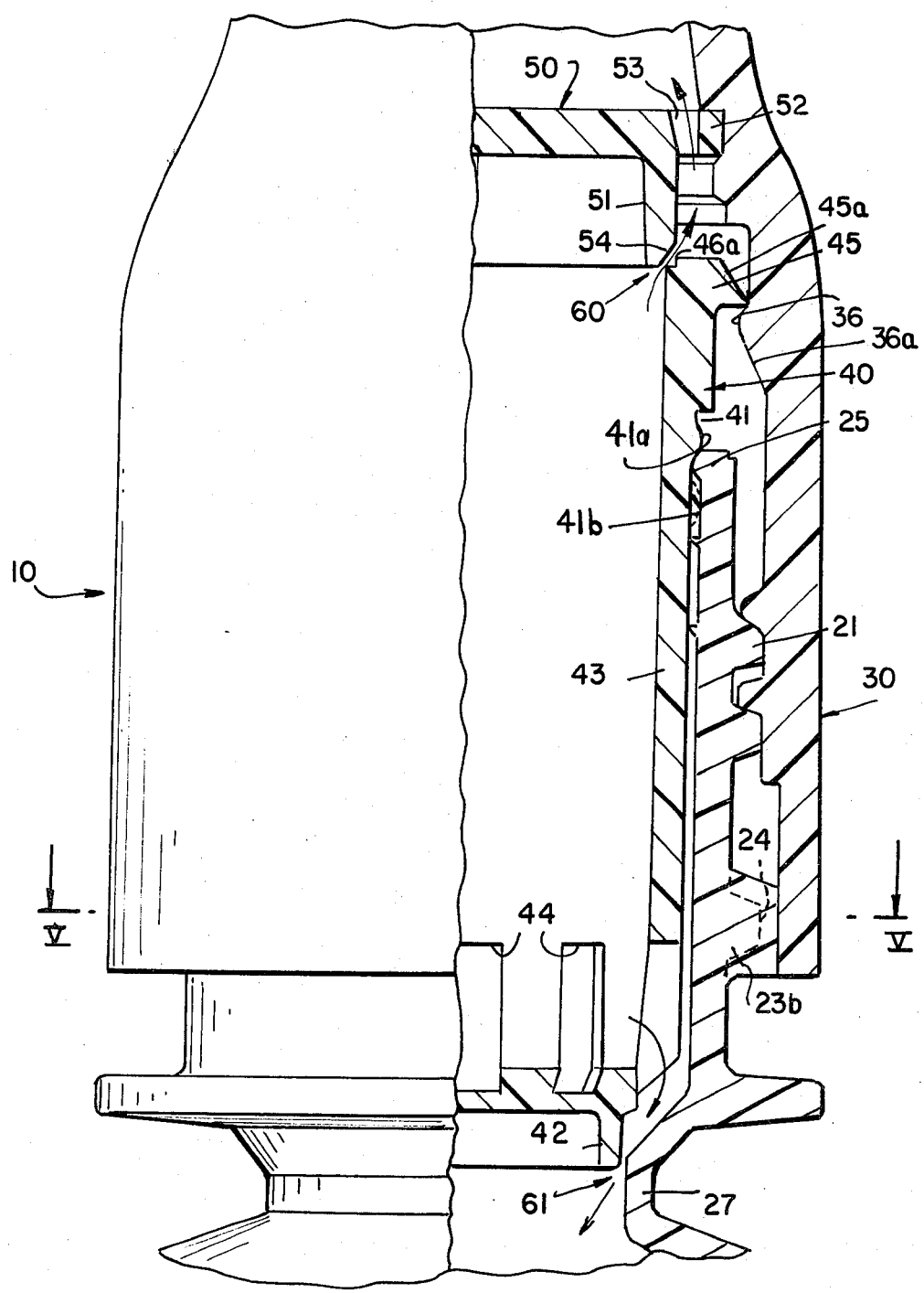
FIG. 3 is a view similar to FIG. 2 showing the reservoir in its open position ready for dispensing.

As seen in FIG. 2, the upper walls of lugs 23a and 23b and the lower walls of lugs 33a and 33b are complementary and are inclined downwardly and away from the bottle as viewed in FIG. 2 to assist in sliding the lugs 33a, 33b over lugs 23a, 23b as the probe 30 is attached to the bottle 20. As best seen in FIG. 3, the wall 45a of flange 45 and the wall 36a of rib 36 are similarly complementary to aid in passing the rib 36 over flange 45 as the probe 30 moves downwardly onto bottle 20.

Bottle 20 is of flexible plastic and may be formed by injection blow-molding. The probe 30, reservoir 40 and sealing fitment 50 are of rigid plastic and may be formed by injection molding.

Douche product 10 is used by rotating probe 30 counterclockwise (as viewed in FIG. 5) relative to the bottle 20. As the probe is rotated to its fully open position shown in FIG. 3, the sealing fitment 50 will rise relative to the reservoir 40 and bottle 20 thus opening the top of reservoir 40. The depth of penetration of wall 51 into the top of reservoir 40 is related to the pitch of thread 21 such that wall 51 is removed from reservoir 40 just before the probe 30 is rotated counterclockwise through 90° (e.g. about 80°) relative to the bottle 30 and reservoir 40. When the fitment 50 is thus removed from the reservoir 40, an annular space is created between the tapered surface 54 (FIG. 3) and the notched inner wall 46a, which serves as a port 60 to permit the flow of liquid from reservoir 40 through ports 53 as shown by the arrows.

During the initial 90° rotation of probe 30, rib 36 (FIG. 2) moves upwardly relative to reservoir 40 until rib 36 contacts the underside of flange 45. Continued counterclockwise rotation of probe 30 relative to the bottle 20 will disengage snap ring 25 from groove 41 and will gradually withdraw reservoir 40 from bottle head 22, with sealing fitment 50 moving at all times with probe 30 thus keeping the port 60 open. Rotation of probe 30 through a total of 180° from its initial, closed position (FIG. 2) will then bring the douche product 10 to its fully open position (FIG. 3).

Probe 30 is threadedly secured to the bottle head 22 by screw thread 21 so that the mechanical advantage provided by the screw can be used to force the fitment 50 into and pull it out of the reservoir 40 as well as to pull the reservoir 40 out of bottle head 22. This ensures proper sealing on assembly and a smooth operation of the delivery of the liquid from the reservoir 40 to the bottle 20.

The pitch of thread 21 is related to the distance between flange 45 and rib 36 so that rib 36 engages flange 45 after fitment 50 has been removed from reservoir 40; thus when reservoir 40 moves relative to the bottle 20, it does not move relative to fitment 50. This ensures that port 60 remains open during the movement of reservoir 40 out of bottle 20.

The pitch of thread 21 is also related to the depth of engagement of base 42 in neck 27 so that base 42 is disengaged from neck 27 to create port 61 when probe 30 is rotated about 180° from its fully closed position, say about 170°. As probe 30 is rotated counterclockwise, lugs 33a and 33b rise from their initial position (FIGS. 2 and 4) towards bottle lugs 23a and 23b (FIGS. 3 and 5) until lugs 33a and 33b are coplanar with and engage lugs 23b and 23a, respectively (FIG. 5). Lugs 23a, 23b, 33a, 33b are a preferred feature to prevent accidental over-rotation and separation of probe 30 from bottle 20. Ring 24 reduces any tendency to override the lugs.

While it is preferred that port 60 is opened after 80°-90° of counterclockwise rotation and port 61 is opened after 170°-180°, other values can be used depending upon the geometry involved. For example, in a given case, it may be desirable to open port 60 very early, in which case only a small amount of rotation of probe 30, say about 20°, will open port 60. In other cases, it may be desirable to open port 60 only after 120° (or more) of rotation. Similarly, the amount of rotation to open port 61 may also be more or less than 170°-180°, as desired.

Probe 30 is provided with apertures 37 (FIG. 1) spaced axially and circumferentially around probe 30. As soon as base 42 of reservoir 40 clears neck 27 to open port 61, atmospheric pressure is applied to the top of the liquid in reservoir 40, through ports 37, 53 and 60, thus causing liquid in reservoir 40 to drain by gravity through outlet ports 44 and port 61 into bottle 20 as shown by the arrows (FIG. 3). The reservoir liquid rapidly mixes with the bottle liquid, with gentle swirling to assist in the mixing, to form a medicated douching liquid. The contents are dispensed by manually squeezing the bottle 20, whereby the liquid will flow from bottle 20 through ports 61 and 44 into reservoir 40, and from reservoir 40 via ports 60 and 53 into the probe 30, whereupon the liquid exits through ports 37.

When the douche product is in the open position, flange 45 bearing on rib 36 and snap ring 25 bearing on the outside of the reservoir body 43 will provide a seal to prevent liquid from leaking out between bottle 20 and probe 30 during dispensing of the contents of bottle 20. Thread 21 is preferably a double lead thread to provide a high degree of friction to prevent backing off of the fully closed probe 30 from the bottle 20 during shipment and handling and to provide some additional sealing surface during dispensing of the liquid.

It is found that nozzle 30 becomes partially unscrewed during shipment, then the top of flange 28 and the bottom of nozzle 30, which seats on flange 28, may each be provided with a pattern of radially disposed sawtooth ridges (not shown) or similar mechanical or frictional engagement means that are disengaged when the user twists open the nozzle 30.

Should the user inadvertently turn the probe 30 clockwise after the product 10 is in the fully open position, the ring 41a (FIG. 6) will provide resistance against the downward movement by engaging the top of head 22. If this resistance is overcome, and the reservoir 40 is completely resealed, then reopening the product 10 will restore the product 10 to its fully open position. However, if the probe 30 is rotated clockwise only slightly, say about one-quarter turn, then the cover 50 will be forced partly into the reservoir 40, with ring 41a remaining above snap ring 25 as shown in FIG. 3, so that counterclockwise rotation of the probe 30 to reopen the product 10 will only move the cover 50 and reservoir 40 upwardly as a closed unit. To prevent this from happening, another ring 41b, shown schematically in dotted line in FIG. 3, may be provided just below and parallel to ring 41a so that snap ring 25 is between the two reservoir rings 41a, 41b when the bottle is in the fully open position. The lower reservoir ring 41b will resist upward movement of the reservoir 40, and will thus allow cover 50 to be pulled out of reservoir 40, when probe 30 is rotated counterclockwise to reopen product 10.

What is claimed:
1. A douche product, which comprises:
   a. an elongated reservoir means having an open end and a closed end, a liquid in said reservoir means, said closed end having port means for permitting the flow of liquid into and out of said reservoir means, a cover means removably mounted in and sealing said open end, and first and second flange means for said cover means and said reservoir means, respectively;

b. a bottle having an elongated head with an opening in said head for permitting the flow of liquid into and out of said bottle, a douching liquid in said bottle, said reservoir means being removably and sealingly mounted in said opening in a normally closed position with said closed end inside said bottle and said cover means outside said bottle, said reservoir means being movable from said closed position to an open position, sealing means engaging said reservoir means when said reservoir means is in said closed position for preventing flow of liquid between said bottle and said reservoir means via said port means;

c. tubular nozzle means threadedly engaging said head and operable to be advanced towards or away from said bottle by rotation of said nozzle means about said head in a first or second direction, respectively, said nozzle means having aperture means therein for permitting liquid to be dispensed from said bottle through said nozzle means; and d. operating means associated with said nozzle means operable when said nozzle means is moved in a predetermined direction relative to said head to move said reservoir means from said closed position to said open position and to remove said cover means from said reservoir means, said operating means comprising (i) securing means for securing said first flange means to said nozzle means, whereby said cover means and nozzle means move as a unit when said nozzle means is rotated, and (ii) flange-engaging means on said nozzle means for engaging said second flange means after said nozzle means has been rotated through a predetermined rotation in said second direction and then moving said reservoir from said closed position to said open position upon further rotation of said nozzle means in said second direction, said sealing means being disengaged from said reservoir means when said reservoir means is in said open position, whereby said liquid in said reservoir means drains into said bottle through said port means, and said reservoir means and cover means being operable when said reservoir means is in said open position and said cover means is removed therefrom to permit dispensing of the contents of said bottle through said nozzle means.

2. Apparatus according to claim 1, wherein said head is connected to said bottle via a neck portion, said port means being within said head when said reservoir is in said closed position, said neck portion being engaged with said reservoir means closed end and thus providing said sealing means when said reservoir is in said closed position and being spaced from said reservoir closed end when said reservoir is in said open position.

3. Apparatus according to claim 2, wherein said securing means and said flange-engaging means are disposed on said nozzle means such that said cover means is spaced from said reservoir open end and said neck portion is spaced from said reservoir closed end when said reservoir is in said open position, and said first flange means is operable to permit liquid dispensed from said reservoir open end to flow through said nozzle means whereby liquid is permitted to be dispensed from said bottle through said nozzle means via said reservoir means.

4. Apparatus according to claim 3, wherein said reservoir means is cylindrical with a circular open end, said cover means has a circular top and a depending circular wall, said circular wall being sealingly press-fit into said reservoir means open end when said reservoir means is in said closed position, and said first flange means extends from said top beyond said circular wall.

5. Apparatus according to claim 4, wherein said first flange means is continuous and has apertures therein permitting flow of liquid therethrough.

6. Apparatus according to claim 4, wherein said first flange means comprises a plurality of spaced flange portions extending from said top, the spaces between adjacent flange portions permitting flow of liquid between said flange portions.

7. Apparatus according to claim 4, wherein said reservoir means has an exterior circular groove adjacent said open end and said head has an interior circular snap ring sealingly engaged in said circular groove when said reservoir means is in said closed position.

8. Apparatus according to claim 7, wherein said snap ring sealingly engages the exterior of said reservoir means when said reservoir is in said open position.

9. Apparatus according to claim 1, wherein said head and said nozzle means have cooperating stop means engageable after said operating means has moved said reservoir means to said open position to prevent further movement of said nozzle means in said predetermined direction.

* * * * *